(12) United States Patent
Muthukumaran et al.

(10) Patent No.: US 7,829,700 B2
(45) Date of Patent: Nov. 9, 2010

(54) PROCESS FOR PREPARATION OF A PHARMACEUTICALLY PURE POLYMORPHIC FORM I OF OLANZAPINE

(75) Inventors: Ganesan Muthukumaran, Tamil Nadu (IN); Kaliyappan Veeramani, Tamil Nadu (IN); Radhakrishnan Selvaraju Mullaiyur, Tamil Nadu (IN); Vedapuri Porchezhiyan, Tamil Nadu (IN); Selvaraj Kanagasalam, Tamil Nadu (IN); Kassim Khan Nazir, Tamil Nadu (IN); T. Chandiran, Chennai (IN)

(73) Assignee: Shasun Chemicals and Drugs Limited, Tamil Nadu (IN)

( * ) Notice: Subject to any disclaimer, the term of this patent is extended or adjusted under 35 U.S.C. 154(b) by 832 days.

(21) Appl. No.: 11/568,422

(22) PCT Filed: Sep. 5, 2005

(86) PCT No.: PCT/IN2005/000298

§ 371 (c)(1),
(2), (4) Date: Dec. 28, 2006

(87) PCT Pub. No.: WO2006/027800

PCT Pub. Date: Mar. 16, 2006

(65) Prior Publication Data

US 2008/0234479 A1    Sep. 25, 2008

(30) Foreign Application Priority Data

Sep. 6, 2004    (IN) .................... 898/04

(51) Int. Cl.
C07D 495/04    (2006.01)
(52) U.S. Cl. .................................... 540/557
(58) Field of Classification Search ........... 540/557
See application file for complete search history.

(56) References Cited

U.S. PATENT DOCUMENTS

| | | | |
|---|---|---|---|
| 5,229,382 | A | 7/1993 | Chakrabarti et al. |
| 5,627,178 | A | 5/1997 | Chakrabarti et al. |
| 5,736,541 | A | 4/1998 | Bunnell et al. |
| 5,744,470 | A | 4/1998 | Tran |
| 5,817,655 | A | 10/1998 | Chakrabarti et al. |
| 5,817,656 | A | 10/1998 | Beasley, Jr. et al. |
| 5,817,657 | A | 10/1998 | Beasley, Jr. et al. |
| 5,929,070 | A | 7/1999 | Shannon et al. |
| 6,008,216 | A | 12/1999 | Chakrabarti et al. |
| 6,020,487 | A | 2/2000 | Bunnell et al. |
| 6,147,072 | A | 11/2000 | Bymaster et al. |
| 6,251,895 | B1 | 6/2001 | Larsen et al. |
| 2001/0020032 | A1 | 9/2001 | Morris et al. |
| 2004/0048854 | A1 | 3/2004 | Patel et al. |

FOREIGN PATENT DOCUMENTS

| | | |
|---|---|---|
| EP | 0733635 B1 | 9/1996 |
| EP | 0830858 A1 | 3/1998 |
| EP | 0830864 B1 | 3/1998 |
| EP | 0831097 B1 | 3/1998 |
| EP | 0831098 B1 | 3/1998 |
| WO | 199630375 A1 | 10/1996 |
| WO | 1997035582 A1 | 10/1997 |
| WO | 1998046230 A1 | 10/1998 |
| WO | 200218390 A1 | 3/2002 |
| WO | 2003055438 A2 | 7/2003 |
| WO | 2003097650 A1 | 11/2003 |
| WO | 2003101997 A1 | 12/2003 |
| WO | 2004056833 A1 | 7/2004 |
| WO | 2004058773 A1 | 7/2004 |

*Primary Examiner*—Brenda L Coleman
(74) *Attorney, Agent, or Firm*—Caesar, Rivise, Bernstein, Cohen & Pokotilow, Ltd.

(57) ABSTRACT

The invention is directed to a novel method for making crystalline Form I of Olanzapine, wherein crude olanzapine is dissolved in a water-miscible solvent in which it is freely soluble, from which substantially pure polymorphic Form I of Olanzapine is recovered by precipitation.

9 Claims, No Drawings

PROCESS FOR PREPARATION OF A PHARMACEUTICALLY PURE POLYMORPHIC FORM I OF OLANZAPINE

This application is a national stage entry under 35 U.S.C. §371 of PCT/IN05/00298, filed Sep. 5, 2005.

FIELD OF THE INVENTION

This invention relates to a novel process for preparation of a pharmaceutically pure polymorphic form I of Olanzapine. More particularly this invention relates to precipitating substantially pure Olanzapine Form I from a solution containing crude olanzapine.

BACKGROUND OF THE INVENTION

The compound 2-methyl-4-(4-methyl-1-piperazinyl)-10H-thieno[2,3-b ][1,5]benzodiazepine [olanzapine] is useful for treating-psychotic patients and mild anxiety states. Preparation of olanzapine and its acid salts having pharmaceutical properties particularly in the treatment of central nervous system disorders has been disclosed in U.S. Pat. No. 5,229,382 (hereinafter referred to as the '382 patent). This patent does not refer to any specific polymorphic crystalline form of olanzapine.

Olanzapine exists in two important polymorphic forms, known as Form I and Form II, distinguishable by X-ray powder diffractometry. EP 733,635 claims Form II of olanzapine and designates the product obtained according to the process described in previous the '382 patent as Form I. It also describes the preparation of Form II olanzapine from ethyl acetate. This patent further adds that anhydrous Form I of olanzapine is metastable and is therefore not well suited for commercial use in pharmaceutical formulations.

However, it has been discovered that anhydrous Form I olanzapine, is stable and is therefore well adapted for commercial use in pharmaceutical formulations. Accordingly there is a need for a process to prepare olanzapine Form I free from the Form II impurity. It is desirable to prepare the substantially pure anhydrous Form I olanzapine to assure uniformity of product.

Although example 1 of the '382 patent discloses a process to obtain olanzapine Form I by recrystallization of olanzapine from acetonitrile, the polymorphic form in these experiments was characterized for its X-ray Powder diffraction and showed that the d values for this product matched with those of olanzapine Form II claimed in EP 733,635. It is therefore inferred that recrystallization of Olanzpine in acetonitrile produces form II and not Form I.

WO 02/18390 discloses a process for the preparation of form I of olanzapine by crystallization of raw olanzapine, olanzapine hydrate or its polymorphic form II from methylene chloride. It has been found that extending the duration of the process of olanzapine crystallization from methylene chloride to yield sufficiently pure final crystalline form I leads to the formation of the additional contaminating compound, especially during heating at reflux temperature. Also repeated crystallization from methylene chloride lead only to a progressive accumulation of the impurity to levels unacceptable in view of the purity requirements for the pharmaceutical materials.

WO03101997 A1 [equivalent to US 2004/0048854 A1] discloses a process of preparation of Form I olanzapine free of the Form II impurity. According to this patent olanzapine is purified in an acidic medium followed by extraction with organic solvents. The resulting mixture is then basified under cold conditions and then extracted using low boiling organic solvents. Further, it discloses that a basic solvent (such as toluene and methanolic sodium hydroxide) is critical to separate out Olanzapine Form I.

WO 03/055438 discloses a process of seeding a solution of an alcoholic solution with substantially pure form I, prior to crystallization to obtain Form I as a product.

Until now, there has been no disclosure of obtaining Olanzapine Form I by precipitation, which generally is a much more simpler technique. Thereby, the inventors of the present application have discovered a novel method for obtaining substantially pure Olanzapine Form I by precipitation technique.

The present invention related to a process for preparation of substantially pure Olanzapine Form I. The polymorphic Form I herein represents the Form I as defined in EP 733,635 and WO96/30375. The X-ray diffractogram of this polymorphic form exhibits the characteristic inter-planar distances d (in angstroms): 9.94, 8.55, 8.24, 6.88, 6.24, 5.58, 5.30, 4.98, 4.83, 4.72, 4.62, 4.53, 4.46, 4.29, 4.23, 4.08, 3.82, 3.74, 3.69, 3.58, 3.50, 3.33, 3.28, 3.21, 3.11, 3.05, 2.94, 2.81, 2.75, 2.65, 2.63, 2.59.

OBJECT OF THE INVENTION

The object of the present invention is to develop a new process for the preparation of substantially pure Form I olanzapine.

Another object of the invention is to develop a new process for the preparation of substantially pure Form I olanzapine by precipitation technique. Form I prepared by the present invention also has satisfactory color and thermal stability for use in pharmaceutical solid dosage form.

SUMMARY OF THE INVENTION

In order to achieve the said object the present invention provides a process for converting crude grade olanzapine into substantially pure Form I olanzapine by precipitation technique. The process involves dissolving crude olanzapine in a water-miscible solvent, and adding water to the solution to precipitate the product The present invention relates to a process for converting crude Olanzapine to substantially pure Form I Olanzapine comprising:
 a) dissolving crude Olanzapine in a solvent,
 b) adding water to precipitate the product, and
 c) recovering substantially pure Olanzapine Form I by filtering the precipitate and drying the said precipitate.

The solvent used for dissolving crude olanzapine is DMSO [dimethyl sulphoxide]. Other solvents that have been used are: DMF [dimethylformamide] & THF [tetrahydrofuran].

The temperature at which water is added is 40° C.-50° C., more preferably at 50° C. An alcoholic solvent is added to the crude olanzapine solution at a temperature of 40° C.-50° C., prior to the addition of water. The alcoholic solvents used are methanol and ethanol. The reaction product is isolated by known techniques such as filtration or centrifugation. The pure Form 1 olanzapine is recovered by isolating and drying the precipitate. Drying of the product is carried out at a temperature of 50° C.-70° C.

DETAILED DESCRIPTION OF THE INVENTION

The compound 2-methyl-4-(4-methyl-1-piperazinyl)-10H-thieno[2,3-b ][1,5]benzodiazepine [olanzapine] is useful for treating psychotic patients and mild anxiety states.

As used herein "substantially pure" refers to Olanzapine associated with less than 5% Form II, and more preferably less than about 1% Form II. Further, "substantially pure" Form I will contain less than 0.5% related substances, wherein "related substances" refers to undesired chemical impurities or residual organic solvent.

As used herein the term "crude" refers to Olanzapine typically associated with undesired polymorph and/or greater than 5% undesired related substances. Such crude grade olanzapine may contain less than 1% undesired related substances.

Compound characterization methods include, for example x-ray powder pattern analysis, differential scanning calorimetry (DSC), and Infrared spectroscopy.

The materials for the present invention can be purchased or prepared by a variety of procedures well known to those skilled in the art. Crude Olanzapine can be prepared as described in U.S. Pat. No. 5,229,382, herein incorporated by reference in its entirety.

The process for converting crude olanzapine to substantially pure Form I olanzapine involves:
  a) dissolving crude olanzapine in a solvent,
  b) adding water to the said solution to form a precipitate, and
  c) recovering substantially pure Form I olanzapine by filtering the precipitate and then drying the precipitate.

Crude olanzapine is dissolved initially in a water-miscible organic solvent. It is preferable to use solvents in which olanzapine is readily soluble such as dimethyl sulpholide (DMSO) to minimize solvent handling. The same objective can be achieved using the other solvents mentioned herein. The solution can be prepared by stirring and/or gentle heating. The solvent can be selected from a group consisting of dimethyl sulfoxide, dimethylformammide, tetrahydrofuran, either singly or in combination.

To this solution, water is added to precipitate the product. Since some exothermicity [40-50C] may be observed, it is preferable to add water slowly while maintaining the temperature of the reaction mass. Once all the product has been precipitated, the reaction mass is cooled, and the product recovered by known isolation techniques such as filtration or centrifugation. The filtered material is then subjected to drying [50°-70° C.] to obtain substantially pure Form I olanzapine.

As a preferred embodiment of the present invention, an alcoholic solvent such as methanol or ethanol, either singly or in combination is added at a temperature 40° C.-50° C., prior to adding water.

Drying can be done either under vacuum or by fluidization. The fluidization method for drying is more efficient for removing water, and dried until the outlet temperature reaches 50° C.-70° C.

The following examples are provided for the purposes of illustration and are not to be construed as limiting the scope of the claimed invention.

EXAMPLE 1

Preparation of Olanzapine Form-I using DMSO, Methanol and Water

35 Kilos of crude Olanzapine was dissolved in 105 liters of dimethyl sulphoxide, and maintained at 50° C. for 30 minutes. The solution was then filtered through a hyflo bed to remove the insolubles. Additionally 35 liters of dimethyl sulphbxide was charged into the reactor, and press the washings through filter into another reactor.

The filtrate was cooled to 40° C., and 350 liters methanol was added slowly while maintaining the temperature between 40 and 50° C. This was followed by slow addition of 105 liters of water while maintaining the temperature between 40 and 50° C. to precipitate Olanzapine completely from the solution. The reaction mass was then cooled to 0-5° C., maintained for 3 hours at the same temperature, filtered and then dried at 60° C.-70° C. in a fluidized bed drier to obtain 25 kilos of final product. The product was identified as substantially pure Form I of Olanzapine by powder X-ray analysis.

EXAMPLE 2

Preparation of Olanzapine Form-I Using Dimethylformamide, Methanol and Water 25 grams of crude olanzapine was dissolved in 125 ml of dimethyl formamide, and heated to 50-55° C. for 30 minutes, to dissolve the crude material. 1 gram activated carbon was added at 50-52° C. and heating was continued. The solution was then filtered through a hyflo bed to remove the insolubles. Now, 25 ml of dimethylformamide was charged into the flask, and the washings were pressed through filter.

The filtrate was cooled, and 375 ml methanol was added slowly while maintaining the temperature between 49 and 54° C. This was followed by slow addition of 75 ml of water while maintaining the temperature between 40 and 50° C. The reaction mass is now cooled to precipitate olanzapine completely from the solution. The reaction mass was then cooled to 0-5° C., maintained for 1.5 hours at the same temperature, and filtered and washed with water [25 ml] and dried at 50° C.-55° C. in a fluidized bed drier until moisture content was below 0.3% to obtain 22 grams of final product. The product was identified as substantially pure Form I of Olanzapine by powder X-ray analysis.

EXAMPLE 3

Preparation of Olanzapine Form-I Using THF, Methanol and Water 25 grams of crude olanzapine was dissolved in 75 mL of tetrahydrofuran, and heated to 40-45° C. for 30 minutes, to dissolve the crude material. 1.0 gm Activated carbon was added at 50-52° C. and heating was continued. The solution was then filtered through a hyflo bed to remove the insolubles. Now, 25 mL of tetrahydrofuran was charged into the flask, and the washings were pressed through filter.

The filtrate was cooled, and 375 ml methanol was added slowly while maintaining the temperature between 43 and 47° C. This was followed by slow addition of 75 ml of water while maintaining the temperature between 37 and 42° C. the reaction mass is now cooled to precipitate Olanzapine completely from the solution. The reaction mass was then cooled to 0-5° C., maintained for 1.5 hours at the same temperature, and filtered and washed with water [25 ml] and dried at 50° C.-55° C. in a fluidized bed drier until moisture content was below 0.3% to obtain 20 grams of final product. The product was identified as substantially pure Form I of Olanzapine by powder X-ray analysis.

The present invention is not to be limited in scope by the specific embodiments and examples, which are intended as illustrations of a number of aspects of the invention and any embodiments which are functionally equivalent are within the scope of this invention. Those skilled in the art will know, or be able to ascertain using no more than routine experimentation, many equivalents to the specific embodiments of the invention described herein.

We claim:

1. A process for converting crude olanzapine to substantially pure Form I olanzapine comprising:
   a) dissolving crude olanzapine in a solvent to provide a crude olanzapine solution,
   b) adding water to said crude olanzapine solution to form a precipitate, and
   c) recovering substantially pure Form I olanzapine by filtering and drying said precipitate.

2. A process as claimed in claim 1, wherein said solvent is one in which crude olanzapine is readily soluble.

3. A process as claimed in claim 1, wherein said solvent is at least one member selected from the group consisting of dimethyl sulfoxide, dimethylformamide and tetrahydrofuran.

4. A process as claimed in claim 1, wherein substantially pure Form I olanzapine is precipitated by adding water.

5. A process as claimed in claim 4, wherein water is added at a temperature of 40°-50° C.

6. A process as claimed in claim 1, wherein drying is performed at a temperature of 50°-70° C.

7. A process as claimed in claim 1, wherein an alcoholic solvent is added to the crude Olanzapine solution, prior to adding water.

8. A process as claimed in claim 7, wherein said alcoholic solvent is at least one member selected from the group consisting of methanol and ethanol.

9. A process according to claim 7, wherein said alcoholic solvent is added at a temperature of 40° C.-50° C.

* * * * *